(12) United States Patent
Strommer et al.

(10) Patent No.: US 9,888,970 B2
(45) Date of Patent: *Feb. 13, 2018

(54) SYSTEMS AND METHODS FOR NAVIGATING A SURGICAL DEVICE

(71) Applicant: St. Jude Medical International Holding S.àr.l., Luxembourg (LU)

(72) Inventors: Gera M. Strommer, Haifa (IL); Uzi Eichler, Haifa (IL); Amit Cohen, Binyamina (IL)

(73) Assignee: St. Jude Medical Internaiional Holding S.àr.l., Luxembourg (LU)

( * ) Notice: Subject to any disclaimer, the term of this patent is extended or adjusted under 35 U.S.C. 154(b) by 117 days.

This patent is subject to a terminal disclaimer.

(21) Appl. No.: 14/585,478

(22) Filed: Dec. 30, 2014

(65) Prior Publication Data

US 2015/0182294 A1    Jul. 2, 2015

Related U.S. Application Data

(63) Continuation of application No. 12/950,841, filed on Nov. 19, 2010, now Pat. No. 8,971,993.

(51) Int. Cl.
*A61B 5/05* (2006.01)
*A61B 19/00* (2006.01)
(Continued)

(52) U.S. Cl.
CPC ............ *A61B 19/5244* (2013.01); *A61B 5/06* (2013.01); *A61B 5/066* (2013.01); *A61B 6/487* (2013.01);
(Continued)

(58) Field of Classification Search
CPC ....... A61B 5/06; A61B 17/3403; A61B 34/20; A61B 2090/3975; A61B 2034/2051
See application file for complete search history.

(56) References Cited

U.S. PATENT DOCUMENTS 4,431,006 A   2/1984   Trimmer
5,005,585 A   4/1991   Mazza
(Continued)

FOREIGN PATENT DOCUMENTS

EP   0555043   8/1993
EP   1184684   3/2002
(Continued)

OTHER PUBLICATIONS

An International Search Report for PCT Application No. PCT/IL2011/050013, dated Mar. 28, 2013.
(Continued)

*Primary Examiner* — Joel Lamprecht
(74) *Attorney, Agent, or Firm* — Dykema Gossett PLLC (57) ABSTRACT

Systems and methods are disclosed for navigating a surgical device toward a target organ in the body of a patient. An example method includes providing a surgical needle and a guide wire, the surgical needle configured for insertion into a vein or a beating heart. The method also includes holding the guide wire within the surgical needle while the surgical needle is inserted into the vein or the beating heart. The method also includes generating output in two modes, the output based on at least one medical positioning system (MPS) sensor on the guide wire, the output corresponding to a position of the surgical needle and the guide wire for navigating the surgical needle and the guide wire toward a target in the vein or the heart. The methods can be carried out directly by a physician or via a computer processor-based surgical system.

19 Claims, 6 Drawing Sheets

(51) Int. Cl.

| | | |
|---|---|---|
| *A61B 5/06* | (2006.01) | |
| *A61B 34/00* | (2016.01) | |
| *A61B 17/22* | (2006.01) | |
| *A61B 6/00* | (2006.01) | |
| *A61B 34/20* | (2016.01) | |
| *A61B 34/10* | (2016.01) | |
| *G01R 33/28* | (2006.01) | |
| *A61B 90/00* | (2016.01) | |
| *A61B 17/34* | (2006.01) | |
| *A61B 17/00* | (2006.01) | |

(52) U.S. Cl.
CPC .............. *A61B 17/22* (2013.01); *A61B 34/00* (2016.02); *A61B 34/10* (2016.02); *A61B 34/20* (2016.02); *A61B 17/3403* (2013.01); *A61B 2017/00247* (2013.01); *A61B 2017/22042* (2013.01); *A61B 2017/22049* (2013.01); *A61B 2034/107* (2016.02); *A61B 2034/2051* (2016.02); *A61B 2090/062* (2016.02); *G01R 33/285* (2013.01)

(56) References Cited

U.S. PATENT DOCUMENTS

| | | | |
|---|---|---|---|
| 5,086,780 | A | 2/1992 | Schmitt |
| 5,251,635 | A | 10/1993 | Dumoulin et al. |
| 5,711,299 | A | 1/1998 | Manwaring et al. |
| 5,983,126 | A | 11/1999 | Wittkampf |
| 6,652,515 | B1 | 11/2003 | Maguire et al. |
| 6,926,674 | B2 | 8/2005 | Tenerz |
| RE39,863 | E | 10/2007 | Smith |
| 7,331,236 | B2 | 2/2008 | Smith |
| 7,343,811 | B2 | 3/2008 | Tenerz |
| 7,632,265 | B2 | 12/2009 | Hauck |
| 8,277,417 | B2 | 10/2012 | Fedinec |
| 8,971,993 | B2 * | 3/2015 | Strommer ............... A61B 17/22 600/407 |
| 2001/0032001 | A1 | 10/2001 | Ricart et al. |
| 2002/0022800 | A1 | 2/2002 | O'Holloran |
| 2002/0143317 | A1 | 10/2002 | Glossop |
| 2004/0087877 | A1 | 5/2004 | Besz |
| 2004/0097805 | A1 | 5/2004 | Verard |
| 2004/0215162 | A1 | 10/2004 | Putz |
| 2005/0004521 | A1 | 1/2005 | Zohmann |
| 2005/0107688 | A1 | 5/2005 | Strommer |
| 2005/0277829 | A1 | 12/2005 | Tsonton et al. |
| 2006/0058647 | A1 | 3/2006 | Strommer et al. |
| 2006/0095066 | A1 | 5/2006 | Chang |
| 2006/0189896 | A1 | 8/2006 | Davis |
| 2007/0085686 | A1 | 4/2007 | Oz |
| 2007/0208252 | A1 | 9/2007 | Makower |
| 2008/0132911 | A1 | 6/2008 | Sobe |
| 2009/0105653 | A1 | 4/2009 | Spenser |
| 2011/0098559 | A1 * | 4/2011 | Besz ....................... A61B 5/06 600/424 |

FOREIGN PATENT DOCUMENTS

| | | |
|---|---|---|
| EP | 1391217 | 7/2003 |
| EP | 11374791 | 1/2004 |
| JP | H08000542 A | 1/1996 |
| JP | H10507104 A | 7/1998 |
| JP | 2003275164 A | 9/2003 |
| JP | 2004275776 A | 10/2004 |
| JP | 2004283601 A | 10/2004 |
| JP | 2008500139 A | 1/2008 |
| JP | 2008539901 A | 11/2008 |
| WO | 9605768 A1 | 2/1996 |
| WO | 9729682 | 8/1997 |
| WO | 02/15973 | 2/2002 |
| WO | 2005112778 A1 | 12/2005 |
| WO | 2006/074510 | 7/2006 |
| WO | 2006090141 | 8/2006 |
| WO | 2006121916 A1 | 11/2006 |

OTHER PUBLICATIONS

Walther, et al. "Minimally Invasive Transapical Beating Heart Aortic Valve Implantation—Proof of Concept", European Journal of Cardio-Thoracic Surgery, Sep. 17, 2010, vol. 31, pp. 9-15.

* cited by examiner

SYSTEMS AND METHODS FOR NAVIGATING A SURGICAL DEVICE

CROSS-REFERENCE TO RELATED APPLICATIONS

The present application is a continuation of U.S. application Ser. No. 12/950,841, filed 19 Nov. 2010, now pending, which is hereby incorporated by reference as though fully set forth herein.

BACKGROUND OF THE INVENTION a. Field of the Invention

This invention relates generally to medical instruments, and, more specifically, to navigating a surgical device toward a target organ in the body of a patient.

b. Background Art

Medical procedures are known in which a surgical device is inserted into a patient's body near a target area, the heart for example, to implant cardiac rhythm devices, replacement heart valves, and the like. In a typical subclavian procedure, a physician uses a surgical needle to puncture the subclavian vein in order to enable access for a guide wire to the heart. In one example procedure, transapical aortic valve implantation (TAVI), this approach requires the insertion of the surgical needle directly into the apex of a beating heart. Such punctures may be complicated in some cases, and involve the risk of lung puncture, as well as other complications. In order to reduce these risks, it is desirable for the physician to know the location and orientation of the tip of the surgical needle, and then to visualize the guide wire as it is navigated within the body of the patient, in order to minimize physical injury to the tissues surrounding the desired organ and ensure that the guide wire reaches the target. Methods for determining the location and orientation of surgical devices are known in the art.

One such method utilizes a fluoropaque marker (e.g., a metallic coil, an active impedance-sensing electrode, and the like) coupled to the tip of the needle and another sensor wound around the tip of a guide wire inserted through the needle and used to deliver a cardiac rhythm device, replacement heart valve, etc. to the desired location within the patient's body. The sensors are visible when exposed to a field of ionizing radiation (e.g., x-rays). A display outputs a visual representation of the needle and the guide wire inside the patient's body based on the position of the sensors under the radiation.

However, these methods require that radiation be used during the entire procedure in order that the sensors generate output indicative of the position of the needle and guide wire throughout the procedure. Accordingly, the physician's hands also must be exposed to radiation during the entire procedure. Even after the needle has been placed, the physician's hands are still exposed to radiation while inserting the guide wire through the needle and navigating the guide wire toward the heart.

Systems and methods are desired which provide the physician with a visualization of the location and orientation of the surgical needle within the body of the patient, in order to minimize physical injury to the organs and surrounding tissues. Systems and methods are also desired which provide the physician with a visualization of the location and orientation of the guide wire within the body of the patient, in order to properly position the guide wire near the target organ. Systems and methods are also desired to achieve these objectives while reducing or altogether eliminating the physician's exposure to radiation during a medical procedure.

BRIEF SUMMARY OF THE INVENTION

It is desirable to provide novel systems and methods for navigating a surgical needle and guide wire toward a target organ in the body of a patient.

In an embodiment, the system includes a needle assembly and a guide wire. The guide wire is provided through a surgical needle of the needle assembly, and can be moved in and moved out of the surgical needle. At least one medical positioning system (MPS) sensor (e.g., metallic coil and/or active impedance-sensing or impedance-sending electrode(s)) provided on the guide wire. The MPS sensor(s) are configured to respond to an electromagnetic- and/or impedance-based field, and may be used with any suitable MPS. In one example, the MPS sensor is located at the tip of the guide wire, and the guide wire may be maintained in a substantially fixed position within the surgical needle during insertion of the surgical needle so that the MPS sensor on the guide wire also corresponds to the tip of the surgical needle.

Prior to and/or during a medical procedure, an image, static or dynamic, is acquired for the area of interest, e.g., a fluoroscopic image, an MRI image or the like. This image may be obtained without the physician being exposed to any radiation. An electromagnetic field generator generates the electromagnetic field in the area of interest. The MPS is coupled with the MPS sensor and with the electromagnetic field generator. The MPS sensor produces an output according to the electromagnetic field. The MPS determines the position (i.e., location and/or orientation) of the surgical needle and the guide wire in a coordinate system respective of the MPS, according to the output of the MPS sensor. In addition, the output from a patient reference sensor attached to the patient's body is used to compute the spatial relationship between the electromagnetic field generator and the patient's anatomy. Any patient movement respective to the patient's position when the image was taken is compensated. The MPS computes continuously the spatial relationship between the electromagnetic field generator and the imaging system to compensate any motion of the imaging system with respect to the electromagnetic field. The MPS produces a visual indication respective of the position of the surgical needle and the guide wire overlaid on the image of the area of interest, to enable navigation of the surgical needle and the guide wire toward the target organ (e.g., the patient's heart).

In accordance with an aspect, a system for navigating a surgical device toward a target in a heart is disclosed. The example system includes a needle assembly with a surgical needle configured to be inserted through a tissue. A guide wire is configured to be inserted through a lumen of the surgical needle. A fastening device is operatively associated with the needle assembly to hold the guide wire in a substantially fixed position within the lumen of the surgical needle during insertion of the surgical needle. An MPS sensor is provided on the guide wire. The MPS sensor produces an output in two modes (discussed in more detail below), the output corresponding to the position of the surgical needle and the guide wire for navigating the surgical needle and the guide wire toward the target.

In accordance with another aspect, a navigation system is disclosed. The example system includes a surgical needle having an outside diameter and an inside diameter, the surgical needle to be inserted into a vein or a heart during a medical procedure. A guide wire is configured to be inserted through the inside diameter of the surgical needle. A fastener is configured to hold the guide wire in the surgical needle when the surgical needle is inserted into the vein or the heart. At least one MPS sensor is provided on the guide wire. The at least one MPS sensor generates output in two modes, the output corresponding to a position of the surgical needle and the guide wire for navigating the surgical needle and the guide wire toward a target in the vein or the heart.

In accordance with a further aspect, a method for navigating a surgical device toward a target organ in the body of a patient is disclosed. An exemplary method includes providing a surgical needle and a guide wire, the surgical needle configured for insertion into a vein or a beating heart. The method also includes holding the guide wire within the surgical needle while the needle is inserted into the vein or the beating heart. The method also includes generating output in two modes, the output based on at least one medical positioning system (MPS) sensor on the guide wire, the output corresponding to a position of the guide wire for navigating the guide wire toward a target in the vein or the heart.

Still other features of systems and methods for navigating a surgical device toward a target organ of the body of a patient are disclosed.

DETAILED DESCRIPTION

Many specific details of certain embodiments are set forth in the following description in order to provide a thorough understanding of such embodiments. One skilled in the art, however, will understand that the present disclosure may have additional embodiments, or that the present disclosure may be practiced without several of the details described in the following description.

The disclosed technique overcomes the disadvantages of the prior art by providing a system including a surgical device with at least one MPS sensor located on a guide wire within a surgical needle. An MPS (e.g., the actual processing and display capability) is coupled with the MPS sensor and with an electromagnetic field generator. The needle assembly is inserted into the body of a patient near a target organ. The guide wire can be moved in and out of the surgical needle. In one example, the guide wire is held in a substantially constant position while the surgical needle is being inserted and advanced into the body of the patient. The guide wire is then released and moved separately from the needle toward the target.

The MPS sensor produces an output according to the electromagnetic field which the electromagnetic field generator generates. The MPS determines the coordinates of the guide wire in a coordinate system respective of the MPS, according to the output of the MPS sensor. The MPS superimposes a representation of the surgical needle and the guide wire, on a prerecorded image of the target organ (e.g., a fluoroscopic image of the heart), according to the coordinates of the guide wire. The term "position" herein below, refers either to the location, to the orientation or both the location and the orientation, of an object in a three-dimensional coordinate system.

Accordingly, the physician may image an area of interest of the patient's body just prior to inserting the surgical needle into the patient's body (e.g., using fluoroscopy or other radiation) to obtain a static or dynamic image of the area of interest (e.g., the heart and surrounding area). The physician does not need to be exposed to the radiation during this imaging. Then the radiation source can be turned off, and an electromagnetic field can be generated while the physician inserts the surgical needle into the patient's body and then navigates the guide wire to the target.

The electromagnetic field generates output corresponding to the position of the MPS sensor. This output can be superimposed on the image so that the position of the surgical needle and the position of the guide wire is visible by the physician dynamically or in real-time. In one example, output is generated in two modes. In a first mode, the output represents the position of the surgical needle as the surgical needle is advanced into the patient's body. In a second mode, the output represents the position of the guide wire as the guide wire is navigated toward the target. It is noted that one or both of the position of the surgical needle and/or the position of the guide wire may be shown superimposed on the image.

Figure 1A:
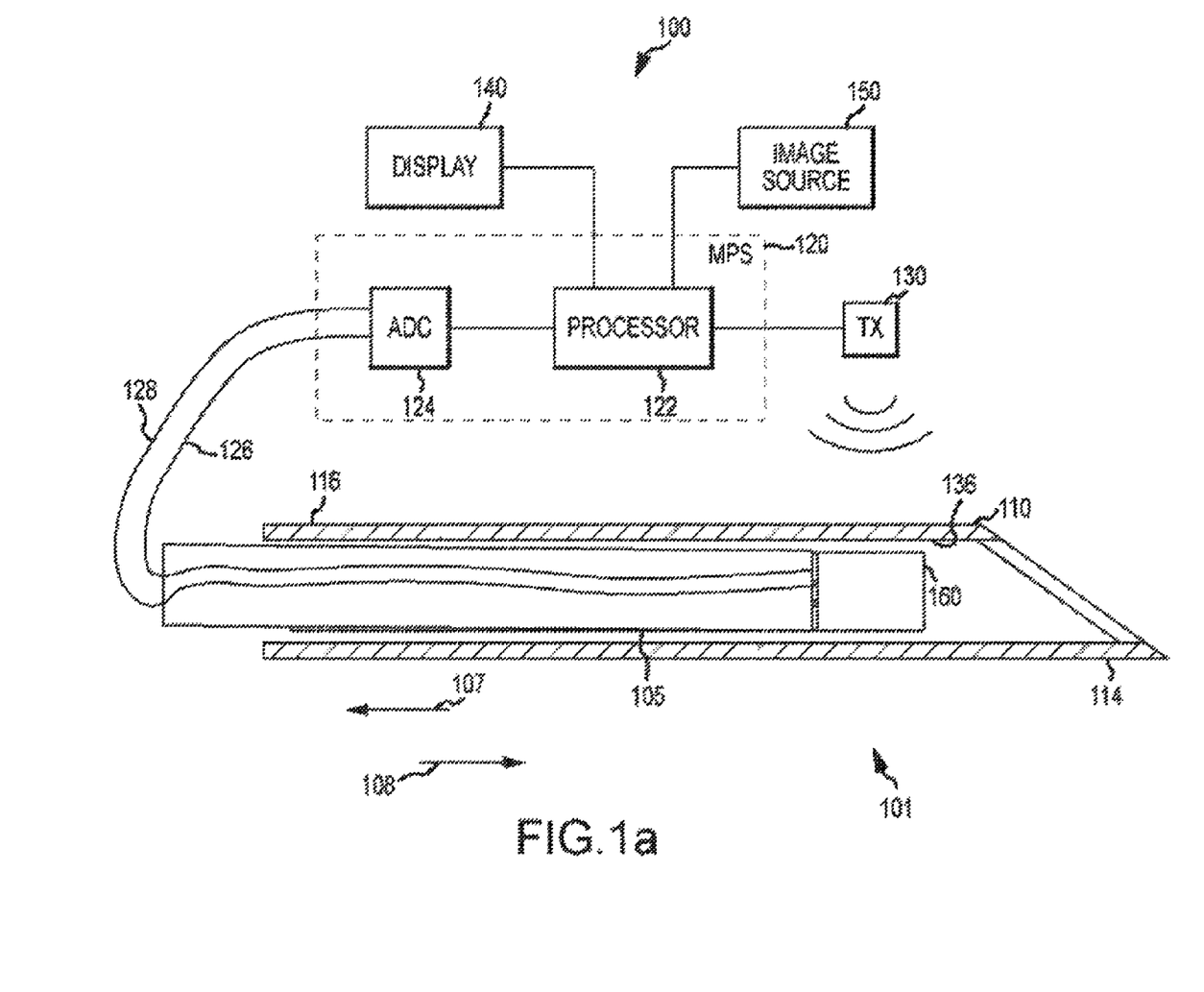
FIGS. 1a-b are high-level schematic illustrations of an embodiment of a system for navigating a surgical device toward a target organ of the body of a patient, wherein (a) a guide wire is shown in a first position retracted within a surgical needle, and (b) the guide wire is shown in a second position extending beyond the tip of the surgical needle.
Figure 1B:
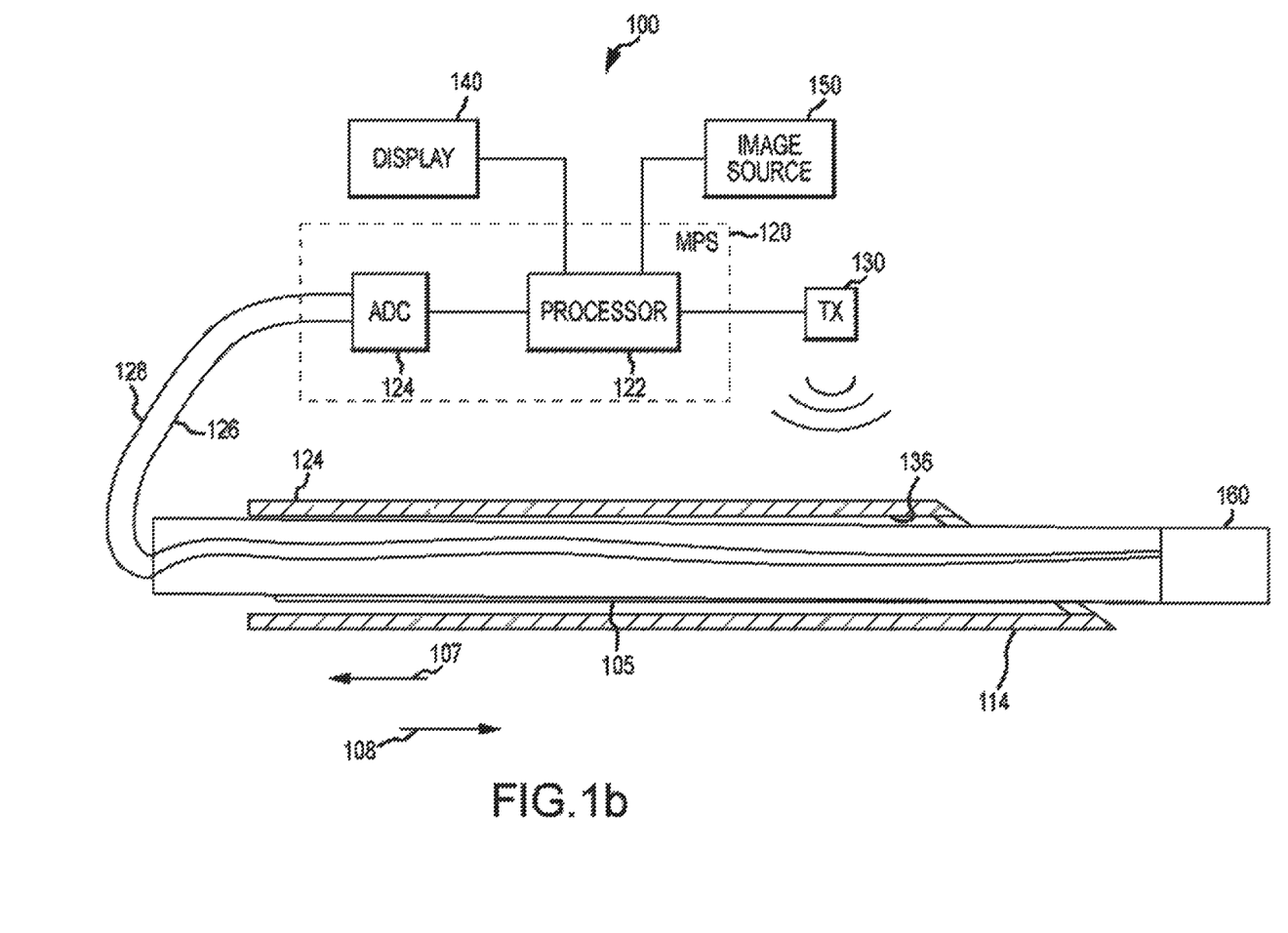

FIGS. 1a-b are high-level schematic illustrations of an embodiment of a system 100 for navigating a surgical device 101 toward a target organ of the body of a patient, wherein (a) a guide wire 105 is shown in a first position retracted within a surgical needle 110, and (b) the guide wire 105 is shown in a second position extending beyond the tip of the surgical needle 110. The surgical needle 110 is shown in a cross-sectional view so that the guide wire 105 can be seen inside of the surgical needle 110. It is noted that the surgical needle 110 and guide wire 105 are shown in exaggerated form in FIGS. 1a-b for purposes of illustration, and are not shown to scale. Surgical needle 110 and guide wire 105 are made of a metal, such as stainless steel, plastic, or the like, and are standard sizes for the desired medical procedure.

The surgical needle 110 and/or guide wire 105 can be disposable in order to prevent transfer of contagious diseases among different patients. In other embodiments, however, guide wire 105 can be reused for performing medical operations on different patients. In this case, the probability of transfer of a virus or a bacterium among patients is reduced, for example, by placing a disposable barrier over the guide wire (e.g., a polymer sheath such as Latex), by sterilizing the guide wire prior to the medical operation, and the like.

FIGS. 1*a-b* show the system 100 including, in addition to the surgical device 101, a medical positioning system (MPS) 120, a magnetic field generator 130, a display 140, and an image source 150. MPS 120 includes a processor 122, and an analog to digital converter (ADC) 124. Processor 122 is coupled with ADC 124, electromagnetic field generator 130, display 140, and with image source 150.

Image source 150 may include a prerecorded image of the organ which is acquired prior to the medical operation on the patient. The prerecorded image may be provided to image source 150 by an imager device, such as computer tomography (CT), magnetic resonance imager (MRI), positron emission tomography (PET), single photon emission computer tomography (SPECT), ultrasound image detector, infrared image detector, X-ray imager (e.g., C-arm), optical coherence tomography (OCT), and the like. The image source 150 can produce a one-dimensional image, a two-dimensional image, or a three-dimensional image of the target organ.

Image source 150 may also produce a different side views (e.g., a right view and a left view) of the target organ, thereby enabling a user to perceive a stereoscopic sensation of the image, by viewing the image on display 140. Once acquired, the imager can be turned off for the remainder of the medical procedure. It is the MPS 120 that is used during the medical procedure to overlay the prerecorded image of the area of interest with a real-time representation of the position of the surgical device 101.

In order to accomplish this, the surgical device 101 may include at least one MPS sensor 160. MPS sensor 160 may include a housing applied over the sensor components which can be in form of an adhesive, plastic tube, elastomeric tube by applying heat, and the like. In an example, the MPS sensor 160 is in the form of a cylinder, although MPS sensor 160 may have any suitable shape and/or configuration. In an example, MPS sensor 160 is in the form of an electromagnetic coil (i.e., a wound wire), which produces an electrical output in response to an electromagnetic field. The housing is made of a metal, such as stainless steel, or the like.

MPS sensor 160 is firmly coupled with the guide wire 105 (e.g., at the tip of the guide wire 105) by methods known in the art, such as welding, brazing, employing an adhesive, pressure fit, and the like. Although only one MPS sensor 160 is shown in FIGS. 1*a-b*, any number of MPS sensors may be provided for the surgical device 101. MPS sensor 160 may also be provided on the surgical needle 110 itself, although as will be better understood from the following discussion, it is not necessary to provide MPS sensors 160 on the surgical needle 110 in order for the surgical needle 110 to be visually represented according to the embodiments described herein.

In an embodiment, the MPS sensor 160 is coupled with ADC 124 by wires 126 and 128. In another example, MPS sensor 160 is in the form of a transmitter and/or receiver. If MPS sensor is a transmitter, then a receiver is provided with the MPS 120; and if the MPS sensor 160 is a receiver, then a transmitter is provided with the MPS 120. The transmitter and receiver may be communicatively coupled to one another by a wireless link, such as Bluetooth, WiFi, Zigbee, IEEE 802 series connections, and the like. The transmitter or receiver may also be physically coupled with guide wire 105, and electrically coupled with the MPS sensor 160.

Still other examples of the MPS sensor 160 are contemplated as being with the scope of the embodiments described herein, and may include sensors, transmitters, and receivers, now known or those later developed, as will be apparent to those having ordinary skill in the art after becoming familiar with the teachings herein. It is noted that the MPS sensor 160 is not limited to a single sensor, or even a single type of sensor. In other embodiments, for example, a plurality of the same type of, or different types of, sensors may be provided.

Secondary sensors may also be utilized. For example, secondary sensors may be provided as one or more radiopaque marker. The radiopaque marker is in the form of a metallic foil, which is visible in an x-ray image thereof (i.e., radiopaque marker fluoresces under x-ray). Temperature and/or pressure sensors may also be provided.

The guide wire 105 and the surgical needle 110 are sized such that an outer diameter of guide wire 105 is less than an inner diameter of a lumen of the surgical needle 110. This enables movement of the guide wire 105 within the lumen of the surgical needle 110, in directions designated by arrows 107 and 108. The user can employ surgical needle 110 to enter the patient's body near a target organ of the patient (e.g., the heart).

In an open-heart or minimally invasive surgical procedure (MIS), when the physician pierces a portion of a target organ of the patient with the surgical needle 110 in order to reach a selected region of the target organ, surgical needle 110 passes through various tissues and fluids, which are located in the vicinity of the target organ. A seal may be provided such that fluids and solid materials which are located at distal portion 114 of the surgical needle 110, cannot reach proximal portion 116 of the surgical needle 110.

In one example, an inner diameter 136 of the surgical needle 110, and an outer (or wire) diameter 126 of guide wire 105 is of such value that the guide wire 105 seals against an inside wall 136 of a lumen of the surgical needle 110. In this manner, the guide wire 105 blocks undesired aspiration of bodily fluids and/or other substances into the lumen of the surgical needle 110 during the procedure. Accordingly, the space shown in FIGS. 1*a-b* between the inner diameter of the surgical needle 110 and the wire diameter of the guide wire 105 is shown in exaggerated form for purposes of illustration. In other examples, however, the outer diameter of the guide wire 105 may be smaller than the inner diameter of the surgical needle 110. In such an example, other means for blocking such undesired aspiration of bodily fluids and/or other substances into the lumen of the surgical needle 110 may be used. Other means may include, for example but not limited to, a mandrel, or a separate seal over one or both end openings of the surgical needle 110.

Before advancing into a portion of an organ of interest (or "target organ") the physician, or a computer processor-based surgical surrogate, moves the guide wire 105 in direction 108 into the lumen of surgical needle 110, such that MPS sensor 160 is located at or near the distal portion 114. In this manner, MPS sensor 160 provides output corresponding to the distal portion 114 of the needle 110 during insertion and while advancing the surgical needle 110 into the patient's body.

In an embodiment, the MPS sensor 160 produces an analog electrical output in response to the electromagnetic field which electromagnetic field generator 130 generates. ADC 124 converts the analog electrical output to a digital format, and provides this digital output to processor 122.

Processor 122 determines the position of the MPS sensor 160, and thus the guide wire 105 in a three-dimensional coordinate system, according to this digital output. Processor 122 can also produce an indication of the position of the tip of surgical needle 110 according to the position of the MPS sensor 160, for the user to navigate surgical needle 110 toward the desired position. These indications of the surgical needle 110 and the guide wire 105 can be seen for example, on display 140.

Display 140 displays a visual indication for the physician (e.g., the visual indication seen in FIGS. 7a-b) by the processor 122 superimposing a representation of the position of the guide wire 105 and the surgical needle 110 on a prerecorded image from image source 150 of the target area.

In a first mode of operation, the guide wire 105 (and hence the MPS sensor 160 on the guide wire 105) is held in a substantially fixed position within the surgical needle 110 while the surgical needle 110 is inserted and advanced into the tissue. Accordingly, the position of the MPS sensor 160 corresponds to the position of the tip of the surgical needle 110 during insertion and advancement. In this manner, the user can view a trajectory of the surgical needle 110 as the user advances surgical needle 110 in the body of the patient toward the target organ. Once the physician ensures that the surgical needle 110 is located at the desired position, the physician can release the guide wire 105 from the surgical needle 110 and move the guide wire 105 (e.g., through a vein) toward the target organ in a second mode of operation.

By viewing the superimposed image on display 140, the physician can verify the position of surgical needle 110 relative to the selected region in or near the target organ. With the aid of this view, the user can maneuver surgical needle 110 and guide wire 105 within the body of the patient, in such a manner that the procedure is minimally invasive and without the physician having to be exposed to radiation during the procedure.

Figure 2A:
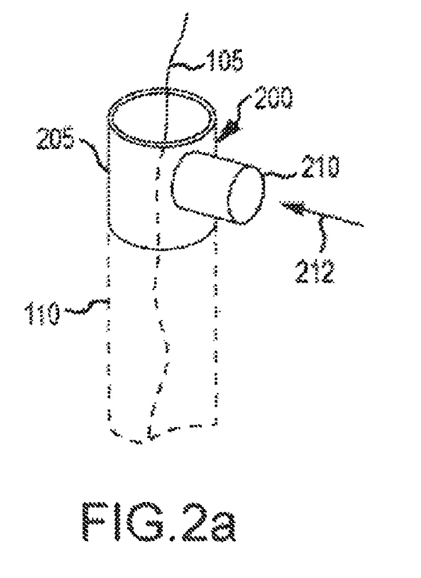
FIGS. 2a-b are perspective views of an embodiment of a fastening device which may be used with the surgical device, showing the fastening device (a) in an open position, and (b) in a closed position.
Figure 2B:
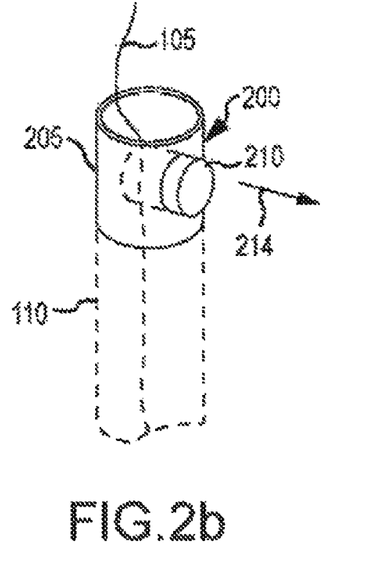

FIGS. 2a-b are perspective views of an embodiment of a fastening device 200 which may be used with the surgical device 101, showing the fastening device 200 (a) in an open position, and (b) in a closed position. In the example shown in FIGS. 2a-b, the fastening device 200 includes a cylindrical coupler 205 which may be connected (e.g., by threading or pressing) to the surgical needle 110. The coupler 205 includes a lumen for receiving the guide wire 105 therethrough.

A plunge assembly 210 is provided on the coupler 205. The plunge assembly 210 may be depressed in the direction of arrow 212 in one direction so that the plunge assembly 210 engages the guide wire 105 and presses the guide wire 105 against an inner side wall of the coupler 205. The plunge assembly 210 may include a tip portion formed of rubber or other pliable material to enhance engagement with the guide wire 105 and the inner side wall of the coupler 205, without deforming the guide wire 105.

Plunge assembly 210 may include a spring-lock mechanism which may be operated similar to a ball point pen (known, and therefore not shown for purposes of simplicity). Alternatively, the plunge assembly 210 may be manually held in the depressed position (e.g., by the physician pressing his or her thumb on the plunge assembly 210). In either case, the guide wire 105 is maintained in a substantially fixed position in at least a portion of the surgical needle 110 by the plunge assembly 210 so that the MPS sensor 160 on the guide wire 105 represents the position of both the guide wire 105 and the surgical needle 110 during insertion and advancement of the surgical needle 110. The plunge assembly 210 may then be moved in the direction of arrow 214 to release the guide wire 105 so that the guide wire 105 can be moved freely within the surgical needle 110 and be navigated within the patient's body (e.g., through a vein).

Figure 3A:
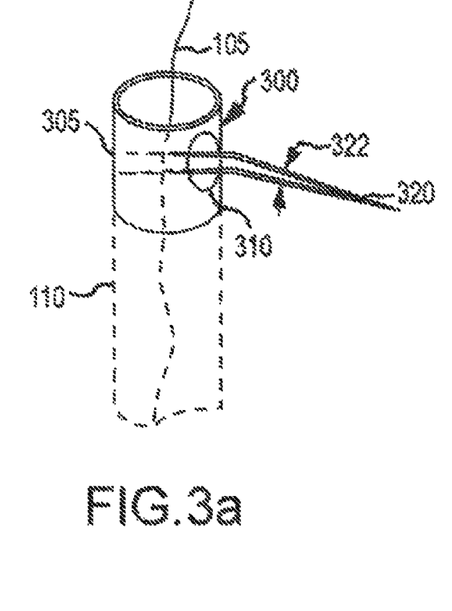
FIGS. 3a-b are perspective views of another embodiment of a fastening device which may be used with the surgical device, showing the fastening device (a) in an open position, and (b) in a closed position.
Figure 3B:
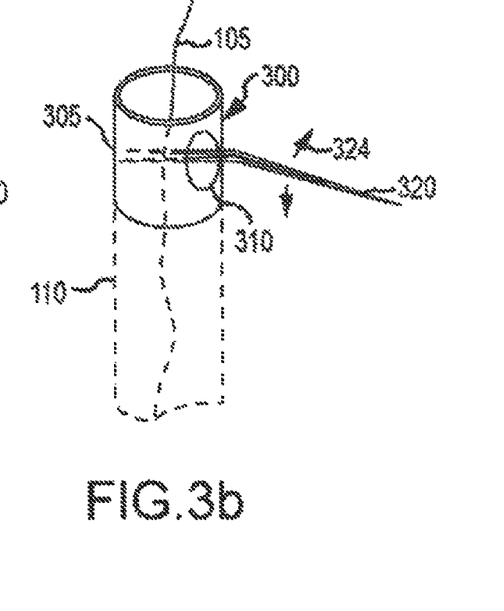

FIGS. 3a-b are perspective views of another embodiment of a fastening device 300 which may be used with the surgical device 101, showing the fastening device 300 (a) in an open position, and (b) in a closed position. In the example shown in FIGS. 3a-b, the fastening device 300 includes a cylindrical coupler 305 which may be connected (e.g., by threading or pressing) to the surgical needle 110. The coupler 305 includes a lumen for receiving the guide wire 105 therethrough.

At least one opening 310 is formed in the coupler 305 such that a securement device 320 may be provided inside the coupler 305. For example, securement device 320 may be tweezers, pliers, or the like. The securement device 320 may be pinched together in the direction illustrated by arrows 322 to engage and hold the guide wire 105 in place. The securement device 320 may include rubber or other pliable material to enhance engagement with the guide wire 105 without deforming the guide wire 105.

The securement device 320 may manually operated to hold the guide wire 105. Alternatively, the securement device 320 may automatically lock in a closed position. In either case, the guide wire 105 is maintained in a substantially fixed position by the securement device 320 so that the MPS sensor 160 on the guide wire 105 corresponds to the position of both the guide wire 105 and the surgical needle 110 during insertion and advancement of the surgical needle 110. The securement device 320 may then be moved in the direction illustrated by arrows 324 to release the guide wire 105 so that the guide wire 105 can be moved freely within the surgical needle 110 and be navigated within the patient's body (e.g., through a vein).

Figure 4A:
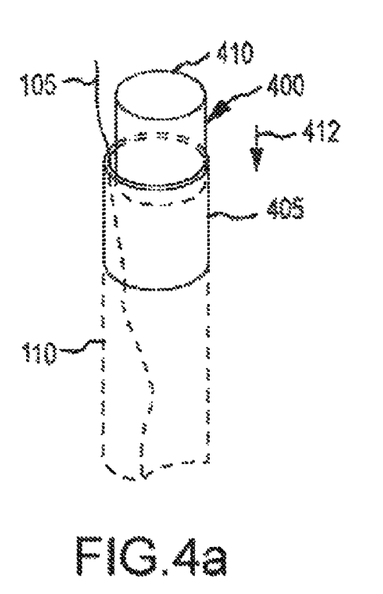
FIGS. 4a-b are perspective views of yet another embodiment of a fastening device which may be used with the surgical device, showing the fastening device (a) in an open position, and (b) in a closed position.
Figure 4B:
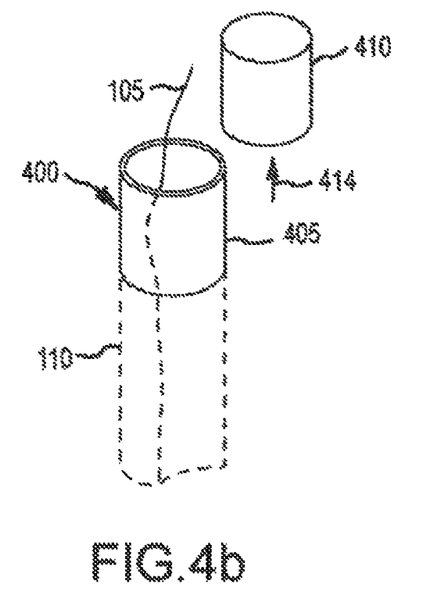

FIGS. 4a-b are perspective views of yet another embodiment of a fastening device 400 which may be used with the surgical device 101, showing the fastening device 400 (a) in an open position, and (b) in a closed position. In the example shown in FIGS. 4a-b, the fastening device 400 includes a collar 405 which may be connected (e.g., by threading or pressing) to the surgical needle 110. The collar 405 includes a lumen for receiving the guide wire 105 therethrough. The fastening device also includes a pliable stopper 410.

In use, the guide wire 105 may first be inserted in the direction illustrated by arrow 412 into the surgical needle 110 through the collar 405. The guide wire 105 is maintained in a substantially fixed position by inserting the pliable stopper 410 into the collar 405 in an orientation that is substantially coaxial to the guide wire 105. Pressing the pliable stopper 410 into the collar 405 adjacent the guide wire 105 holds the guide wire 105 in a substantially fixed position so that the MPS sensor 160 on the guide wire 105 corresponds to the position of both the guide wire 105 and the surgical needle 110 during insertion and advancement of the surgical needle 110. The pliable stopper 410 may then be moved in the direction illustrated by arrow 414 to release the guide wire 105 so that the guide wire 105 can be moved freely within the surgical needle 110 and be navigated within the patient's body (e.g., through a vein).

Figure 5A:
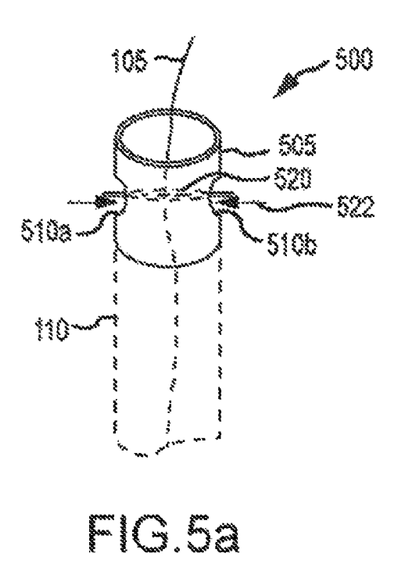
FIGS. 5a-b are perspective views of still another embodiment of a fastening device which may be used with the surgical device, showing the fastening device (a) in an open position, and (b) in a closed position.
Figure 5B:
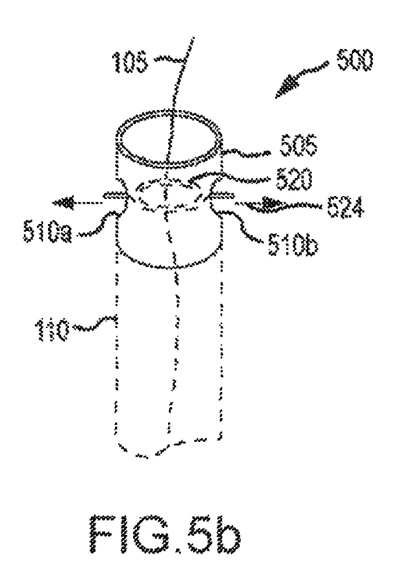

FIGS. 5a-b are perspective views of still another embodiment of a fastening device 500 which may be used with the surgical device, showing the fastening device (a) in an open position, and (b) in a closed position. In the example shown in FIGS. 5a-b, the fastening device 500 includes a collar 505 which may be connected (e.g., by threading or pressing) to the surgical needle 110. The collar 505 includes a lumen for receiving the guide wire 105 therethrough.

At least one opening 510*a-b* is formed in the collar 505 such that a securement device 520 may be provided inside the collar 505. For example, securement device 520 may be a pliable bow element. The securement device 520 may be pinched together in the direction illustrated by arrows 522 to form an opening between the bow-like elements of the securement device 520. The securement device 520 may then be released in the direction illustrated by arrows 524 to engage and hold the guide wire 105 in place. The securement device 520 may include rubber or other pliable material to enhance engagement with the guide wire 105 without deforming the guide wire 105.

The guide wire 105 is "pinched" and maintained in a substantially fixed position by the securement device 520 so that the MPS sensor 160 on the guide wire 105 corresponds to the position of both the guide wire 105 and the surgical needle 110 during insertion and advancement of the surgical needle 110. The securement device 520 may then be opened to release the guide wire 105 so that the guide wire 105 can be moved freely within the surgical needle 110 and be navigated within the patient's body (e.g., through a vein).

It is noted that the examples described above with reference to FIGS. 2*a-b* through 5*a-b* are provided as only as some possible examples of devices which may be used to secure and maintain the position of the guide wire 105 relative to the surgical needle 110. These examples are not intended to be limiting, and other embodiments are also contemplated, as will be apparent to those having ordinary skill in the art after becoming familiar with the disclosure herein.

Figures 6A, 6B:
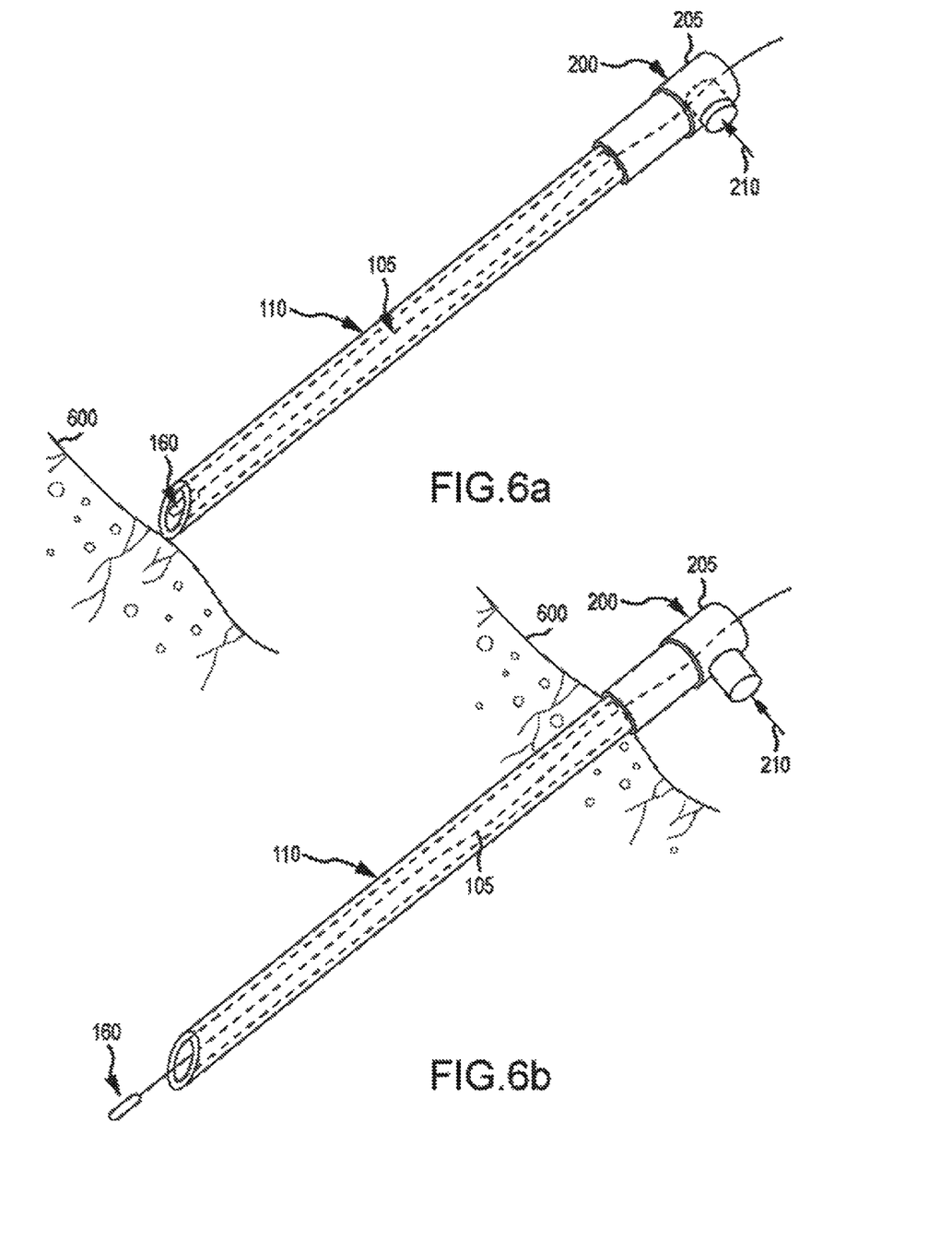
FIGS. 6a-b are perspective views of an embodiment of a surgical device which may be navigated toward a target organ of the body of a patient, showing (a) a position of the guide wire during insertion of the surgical needle into the patient's body, and (b) another position of the guide wire after the surgical needle has been inserted.

FIGS. 6*a-b* are perspective views of an embodiment of a surgical device 101 which may be navigated toward a target organ of the body of a patient, showing (a) a first position of the guide wire 105 during insertion and advancement of the surgical needle 110 into the patient's body, and (b) a second position of the guide wire 105 after the surgical needle 110 has been inserted. The surgical device 101 shown in FIGS. 6*a-b* includes the surgical needle 110, the guide wire 105, and the fastening device 200 shown in FIGS. 2*a-b* (although any embodiment of the fastening device may be provided).

In FIG. 6*a*, the surgical needle 110 is shown positioned adjacent the patient's tissue 600, and the guide wire 105 is in a locked position such that the guide wire 105 (and hence the MPS sensor 160) is maintained in a substantially fixed position relative to the surgical needle 110. In FIG. 6*b*, the surgical need 110 is shown after it has been inserted into the patient's tissue 600. After full insertion (or insertion to the desired position), the guide wire 105 may be released (e.g., by operating fastening device 200) so that the guide wire 105 can be moved independently of the surgical needle 110 and navigated toward a target organ of the body of the patient (e.g., through a vein). An example of visual output generated using the MPS sensor 160 in two separate modes of operation during such a procedure (e.g., insertion and advancement of the surgical needle 110 shown in FIG. 6*a*; and independent positioning of the guide wire 105 shown in FIG. 6*b*) is described in more detail below with reference to the display images shown in FIGS. 7*a-b*.

Figure 7A:
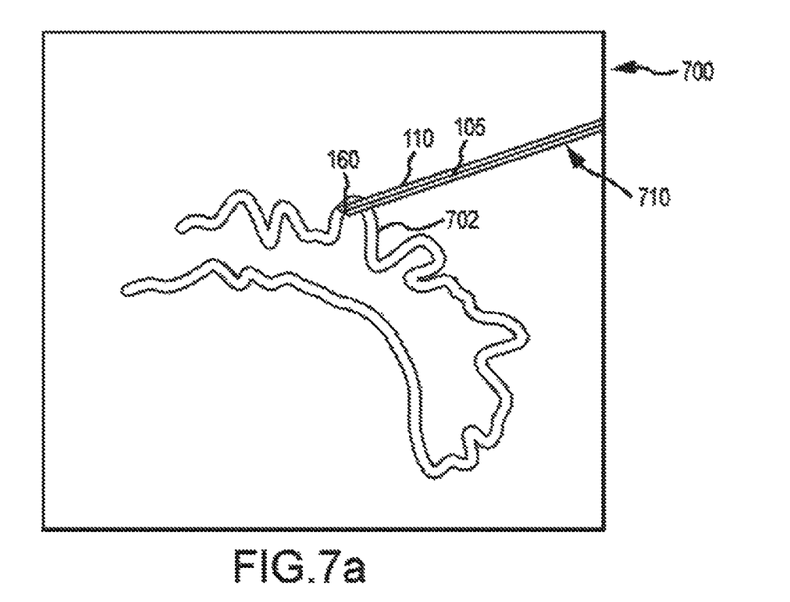
FIGS. 7a-b are example display images illustrating output of the system for navigating a surgical device toward a target organ of the body of a patient, showing (a) operation in a first mode, and (b) operation in a second mode.
Figure 7B:
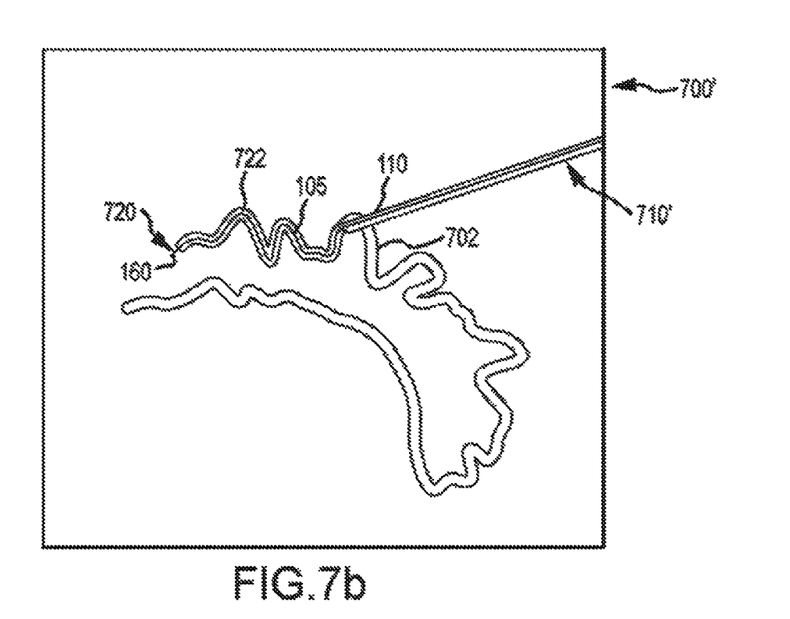

FIGS. 7*a-b* are example display images 700 and 700' illustrating output of the system for navigating a surgical device 101 toward a target organ of the body of a patient, showing (a) operation in a first mode, and (b) operation in a second mode. In the example shown in FIGS. 7*a-b*, the display images 700 and 700' are fluoroscopy images showing the patient's veins 702 in a target area (e.g., in or near the patient's heart). The fluoroscopy images are prerecorded and static so that the physician does not need to be exposed to radiation during the procedure. A graphical representation of the needle 110 and the guide wire 105 obtained based on the MPS sensor 160 are overlaid on the fluoroscopy images as output for the physician.

In an example procedure, the graphical representation of the needle 110 and the guide wire 105 are generated as follows. An electromagnetic field is generated (e.g., electromagnetic field generator 130 shown in FIGS. 1*a-b* generates the electromagnetic field). In response, the MPS sensor 160 produces an analog electrical output signal.

The coordinates respective of the position of the guide wire 105 are determined, in a coordinate system respective of the MPS 120, according to the output of the MPS sensor 160. With reference to FIG. 1, ADC 124 converts the analog electrical output signal produced by the MPS sensor to a digital format. Processor 122 determines the position of the MPS sensor 160 relative to the display images 700 and 700', and thus displays the position of the MPS sensor 160, in an MPS coordinate system respective of MPS 120, according to the electrical output of the MPS sensor 160, in digital format.

A graphical representation 710 of the position of the MPS sensor 160 may be produced in a first mode, to enable navigation of the surgical needle 110 toward the target organ. It is noted that in this first mode, the position of the MPS sensor 160 corresponds to the position of the tip of the surgical needle 110 because the guide wire 105 is being held in a substantially fixed position within the surgical needle 110. Therefore, processor 122 superimposes the graphical representation 710 of the position of the surgical needle 110, in an MPS coordinate system of MPS 120, on an image 700 of the target organ, and directs display 140 to display this superimposed image 700 during insertion and advancement of the surgical needle 110.

By viewing the superimposed image 700 on display 140, the physician can verify the position surgical needle 110 relative to the selected region within the target organ. Once the physician ensures that the tip of surgical needle 110 is located at the desired position based on the position of the graphical representation 710, the physician can release the guide wire 105 from the surgical needle 110 so that the guide wire 105 moves independently of the surgical needle 110, and can be navigated (e.g., through the vein 702) toward the target organ.

Accordingly, the MPS sensor 160 produces output in the first mode (illustrated by the output 700 shown in FIG. 5*a*) corresponding to a position of the surgical needle 110 during insertion and advancement of the surgical needle 110 into the patient's body. The position of the MPS sensor 160 may also be used to produce output in a second mode (illustrated by the output 700' shown in FIG. 7*b*) corresponding to the position of the guide wire 105 in real-time during navigation. In this second mode, the position of the surgical needle 110 may continue to be displayed for the physician, as represented by line 710' in FIG. 7*b*.

After insertion, however, the processor 122 does not need to continue receiving data from the MPS sensor 160 in order to represent the final position of the surgical needle 110. Because the surgical needle 110 is rigid in structure, and its position remains fixed after the insertion procedure, the processor may be configured to sample two points and draw a straight line between two coordinates. That is, the processor may use the point of insertion of the surgical needle 110 into the patient's body, and the end point after advancement of the surgical needle 110. The processor then draws a line between these two points to generate the graphical representation 710' of the surgical needle 110 shown in FIG. 7*b*.

Accordingly, the surgical needle 110 does not need to have its own separate MPS sensor in order for a graphical representation 710' of the surgical needle 110 to continue to be shown on the display.

It is noted that in an embodiment, the graphical representation of the surgical needle 110 may be changed in the second mode so as not to confuse the physician during navigation of the guide wire 105. For example, the graphical representation of the surgical needle may be shown in one color (e.g., red at 710) in the first mode (in FIG. 7a), and then changed to a different color (e.g., blue at 710') in the second mode (in FIG. 7b).

In the second mode, the guide wire 105 is released from the surgical needle 110 and navigated (e.g., through the vein 502) toward the target organ. During movement of the guide wire 105, the MPS sensor 160 produces output substantially in real-time to show dynamic positioning of the guide wire 105.

In the second mode, the processor 122 may be configured to show a graphical representation 720 of the position of the guide wire 105, and may be updated on the display 140 in real-time as the guide wire 105 is moved. The processor 122 may also be configured to show the path 722 that the guide wire 105 has taken. Although only one MPS sensor 160 may be provided, the processor may use historical data (e.g., the previous positions of the MPS sensor 160) to generate a graphical representation of the path 720 of the guide wire 105.

In one embodiment, the graphical representation 720 of the guide wire 105 itself (e.g., the tip of the guide wire 105) is overlaid on the static image along with the path 722 in the same display image 700'. In another embodiment, the guide wire 105 may be rendered using a different color than the color used to represent the path 722.

Although several embodiments of this invention have been described above with a certain degree of particularity, those skilled in the art could make numerous alterations to the disclosed embodiments without departing from the spirit or scope of this invention. References are only used for identification purposes to aid the reader's understanding of the present invention, and do not create limitations as to the position, orientation, or use of the invention. It is intended that all matter contained in the above description or shown in the accompanying drawings shall be interpreted as illustrative only and not limiting. Changes in detail or structure can be made without departing from the spirit of the invention as defined in the appended claims.

The invention claimed is:

1. A system, comprising:
   a first medical device having a longitudinal lumen;
   a second medical device releasably positioned in the longitudinal lumen of the first medical device, the second medical device having a distal portion maintained proximate a distal end of the first medical device in a first mode of operation, and released from the distal end of the first medical device in a second mode of operation; and
   an electromagnetic sensor coupled to the distal portion of the second medical device, wherein a location of the electromagnetic sensor identifies a location of the distal end of the first medical device when in the first mode of operation, and further identifies a location of the distal portion of the second medical device as it moves beyond the distal end of the first medical device when in the second mode of operation.

2. The system of claim 1, wherein the first medical device comprises a surgical needle, the second medical device comprises a guide wire, and wherein the guide wire is releasably positioned in the longitudinal lumen of the needle.

3. The system of claim 1, further comprising an electromagnetic field generator configured to receive the output from the electromagnetic sensor and generate visual feedback showing a position of the system overlayed on a recorded image.

4. The system of claim 1, wherein the electromagnetic sensor produces output substantially in real-time to show dynamic positioning of the second medical device.

5. The system of claim 1, further comprising a plurality of electromagnetic sensors on the second medical device, the plurality of electromagnetic sensors corresponding to separate portions of the second medical device.

6. The system of claim 1, wherein the output of the electromagnetic sensor is generated using an electromagnetic field and superimposed on a static fluoroscopy image.

7. The system of claim 1, further comprising a fastening device operatively coupled to the first and second medical devices to maintain the distal portion of the second medical device proximate the distal end of the first medical device when in the first mode of operation.

8. The system of claim 7, wherein the fastening device comprises a release mechanism configured to release the second medical device from its maintained position and enable movement of the second medical device beyond the distal end of the first medical device when in the second mode of operation.

9. An apparatus, comprising:
   a needle having a longitudinal lumen, and a piercing end configured to penetrate tissue;
   a guide wire releasably coupled to the needle, a distal portion of the guide wire maintained proximate the piercing end of the needle in a first mode of operation, and released from the piercing end of the needle in a second mode of operation; and
   an electromagnetic sensor coupled to the distal portion of the guide wire, wherein a location of the electromagnetic sensor identifies a location of the piercing end of the needle when in the first mode of operation, and identifies a location of the distal portion of the guide wire as it moves beyond the piercing end of the needle when in the second mode of operation.

10. The apparatus of claim 9, further comprising a medical positioning system (MPS) configured to receive the output from the electromagnetic sensor and generate visual feedback showing a position of the apparatus in a pre-recorded image.

11. The apparatus of claim previously presented 9, wherein the electromagnetic sensor produces output in the first mode of operation corresponding to a position of the needle as the needle is inserted into tissue, and the electromagnetic sensor produces output in the second mode of operation corresponding to positioning of the guide wire.

12. The apparatus of claim 9, further comprising a plurality of electromagnetic sensors on the guide wire, the plurality of electromagnetic sensors corresponding to separate portions of the guide wire.

13. The apparatus of claim 9, wherein the output of the electromagnetic sensor is generated using an electromagnetic field and superimposed on a static fluoroscopy image.

14. The apparatus of claim 9, further comprising a fastening device coupled to the needle and the guide wire to maintain the distal portion of the guide wire proximate the distal end of the needle when in the first mode of operation.

15. The apparatus of claim 9, wherein the fastening device comprises a release mechanism configured to release the guide wire from its maintained position and enable its movement beyond the distal end of the needle when in the second mode of operation.

16. The apparatus of claim 9, wherein the needle is configured to be inserted into a heart chamber for transapical valve implantation.

17. The apparatus of claim 9, wherein the needle is configured to be inserted as a subclavian puncture for a cardiac rhythm implantable device, wherein leads are configured to be inserted through the needle and navigated into the heart through the subclavian vein.

18. A method for navigating a surgical device, including a surgical needle and a guide wire, toward a target organ in the body of a patient, the method comprising:
   maintaining a distal end of the guide wire within a lumen of the surgical needle and proximate a distal portion of the surgical needle using a releasable engagement mechanism;
   generating first output in a first mode when the releasable engagement mechanism is selected to maintain the distal end of the guide wire proximate the distal portion of the surgical needle;
   generating second output in a second mode when the releasable engagement mechanism is selected to release the distal end of the guide wire from its position proximate the distal portion of the surgical needle;
   generating an image of the progressive movement of the surgical needle using the first output when in the first mode; and
   generating an image of the progressive movement of the guidewire relative to the surgical needle using the second output when in the second mode.

19. The method of claim 18, further comprising superimposing the position of the surgical needle and the position of the guide wire over a static image.

\* \* \* \* \*